United States Patent [19]

Braden

[11] Patent Number: 4,692,284

[45] Date of Patent: Sep. 8, 1987

[54] METHOD AND APPARATUS FOR FORMING DROPLETS AND MICROCAPSULES

[75] Inventor: William I. Braden, Norfolk, Mass.

[73] Assignee: Damon Biotech, Inc., Needham Heights, Mass.

[21] Appl. No.: 857,854

[22] Filed: Apr. 30, 1986

[51] Int. Cl.⁴ .......................... A61K 9/62; B01J 13/02; B28B 1/54
[52] U.S. Cl. ......................................... 264/4.3; 264/4; 424/93; 424/455; 424/461; 425/5; 425/804
[58] Field of Search ................. 264/4, 4.3; 425/5, 804; 424/455, 461

[56] References Cited

U.S. PATENT DOCUMENTS

| | | | |
|---|---|---|---|
| 2,929,106 | 3/1960 | Snow | 264/14 |
| 3,015,128 | 1/1962 | Somerville, Jr. | 425/5 |
| 3,274,642 | 9/1966 | Cramer | 18/2.7 |
| 3,463,842 | 8/1969 | Flack et al. | 264/0.5 |
| 3,464,926 | 9/1969 | Vandegaer et al. | 425/5 X |
| 3,817,502 | 6/1974 | Taylor | 266/34 R |
| 4,352,883 | 10/1982 | Lim | 264/4 X |
| 4,386,895 | 6/1983 | Sodickson | 425/5 |

Primary Examiner—Richard D. Lovering
Attorney, Agent, or Firm—Lahive & Cockfield

[57] ABSTRACT

A method and apparatus for forming microcapsules from a fluid medium containing living culture material by the atomization of the medium and the treatment of the atomized droplets with a treatment fluid. A medium under pressure enters a chamber having a wall with a plurality of orifices formed therein. A vibrator vibrates the chamber. As the medium passes through the orifices the exit stream vibrates and forms small droplets. The droplets fall into a collection vessel on the other side of the wall, which contains treatment fluid for hardening the droplets into microcapsules. A flow of treatment fluid may be maintained through the collection vessel to prevent clumping of the droplets and to transport the hardened microcapsules for harvesting. Preferred operating pressures, orifice size and chamber configuration are shown.

16 Claims, 3 Drawing Figures

METHOD AND APPARATUS FOR FORMING DROPLETS AND MICROCAPSULES

TECHNICAL FIELD

The present invention relates to the production of small droplets from a fluid medium, and more particularly to the production of such droplets from a culture medium, and the treatment thereof with a second fluid so as to form microcapsules.

The encapsulation of biological material has become a valuable tool in the fields of microbiology, genetic engineering, immunization, and the medical treatment of tissue. Such encapsulation involves the formation of droplets containing substances such as micro-organisms or live cell culture material, and the treatment of the droplets to form capsules thereof without injury of the encapsulated material. An example of this general technique is shown in U.S. Pat. No. 4,352,883, the disclosure of which is incorporated herein by reference.

One apparatus for the formation of such encapsulated material in a production line process is shown in U.S. Pat. No. 4,386,895, of Lester A. Sodickson. In that apparatus, a reservoir of biological medium is centrally located and surrounded by a reservoir of a gelling or hardening agent. The central reservoir rotates, forcing the medium through bundles of hollow outflow needles, similar to hypodermic needles, spaced about its periphery. As the medium flows out through the needles, it is atomized and received in the outer reservoir, where the atomized droplets of medium gel and harden into microcapsules. The inner diameter of the needles is chosen, in relation to the viscosity and other properties of the medium, so as to form droplets which are small enough to not disintegrate upon ejection into the treating agent of the outer reservoir. It is also possible to eject the atomized medium into a gas transport flow, or to have an impinging circumferential gas jet to facilitate the atomization process. One production line system currently employed produces droplets having a diameter of 600 microns with a size distribution of 200-300 microns above and below that size.

OBJECTS AND SUMMARY OF INVENTION

It is an object of the present invention to provide an apparatus and method for the production of microcapsules at a high production rate.

It is another object of the invention to provide an apparatus and method for the production of microcapsules having a substantially uniform and small size.

It is another object of the invention to provide an apparatus and method for the production of microcapsules in which atomized droplets are produced while avoiding clumping of the droplets.

It is another object of the invention to provide an apparatus and method for the production of microcapsules in which atomized droplets are delivered to a treatment fluid and in which the droplets are formed of a size sufficiently small to avoid disintegration thereof on contact with the treatment fluid.

It is another object of the invention to provide an apparatus and method for the production of microcapsules which substantially avoids injury to biological growth material encapsulated therein.

These and other objects of the invention are realized in a method and apparatus for forming microcapsules from a fluid medium by the atomization of the medium and the treatment of the atomized droplets with a treatment fluid. The medium under pressure enters a chamber having a wall with a plurality of orifices formed therein. A vibrator vibrates the chamber, and the medium passes through the orifices, forming small droplets. The droplets fall into a collection vessel containing treatment fluid on the other side of the wall. Preferably, the pressure in the first chamber is selected to optimize the rate of droplet formation. A flow of treatment fluid may be maintained through the collection vessel to prevent clumping of the droplets and to transport the hardened microcapsules to a separation station.

BRIEF DESCRIPTION OF THE DRAWINGS

These and other features of the invention will be understood by reference to the figures, in which.

DETAILED DESCRIPTION

Figure 1:
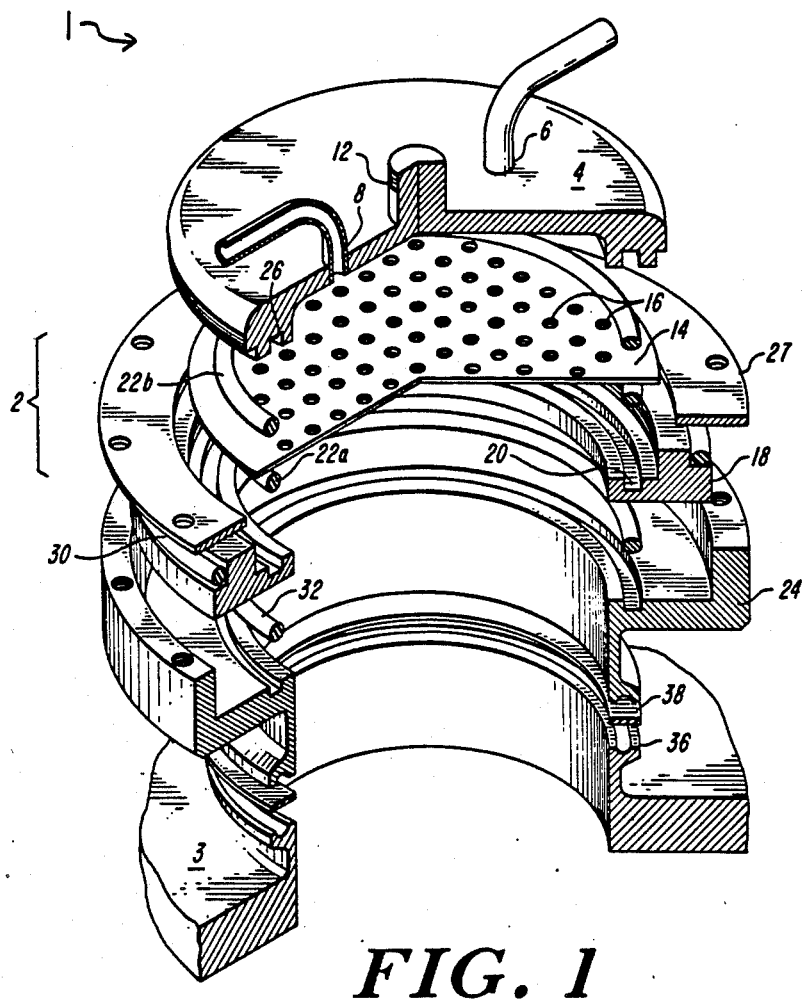
FIG. 1 shows a perspective exploded view of a presently preferred embodiment of apparatus according to the invention.

FIG. 1 shows an exploded perspective view of an apparatus 1 for the production of droplets from a biological medium according to a presently preferred embodiment of the invention. A supply chamber 2 receives a flow of the medium and forms droplets which fall into a collection vessel 3. Supply chamber 2 includes a cap member 4 having an inlet port 6, for providing a flow of the medium, and an outlet port 8. Outlet port 8 serves as a bleeder for trapped air, and is useful in cleaning the apparatus. A vibrator 10 (shown in FIG. 2) attaches to the cap via a coupling 12. Sealed across a lower portion of the cap and forming a wall thereof so as to define the supply chamber is an orifice member 14 having a plurality of holes 16 formed therein.

In the preferred embodiment, the holes 16 have a uniform diameter of approximately 300 microns, and are formed on a grid pattern with a spacing of approximately 5 millimeters. Preferably, the orifice member is sheet titanium, approximately 0.25 millimeters thick, or is made of other hard durable material. Thus, a circular orifice member having a diameter of 10 centimeters, may have several hundred or more holes 16. Preferably the holes are chemically etched. Alternatively, they may be formed by vaporization of the material therein with a laser drilling apparatus. A collar 18 having an annular groove 20 therein for receiving an O-ring 22a is fitted to the cap 4 for securing the orifice member in position. A second O-ring 22b, fitted in a similar groove 26 in the cap, provides a seal on the opposite side of the orifice member.

In this manner, member 14 is removably mounted in the cap, and can be conveniently interchanged with orifice members having different size holes for forming droplets of a different diameter, or for use with a medium of different viscosity. In the example discussed below, a hole size of approximately one-half of the desired droplet diameter has been found to yield excellent results.

Figure 2:
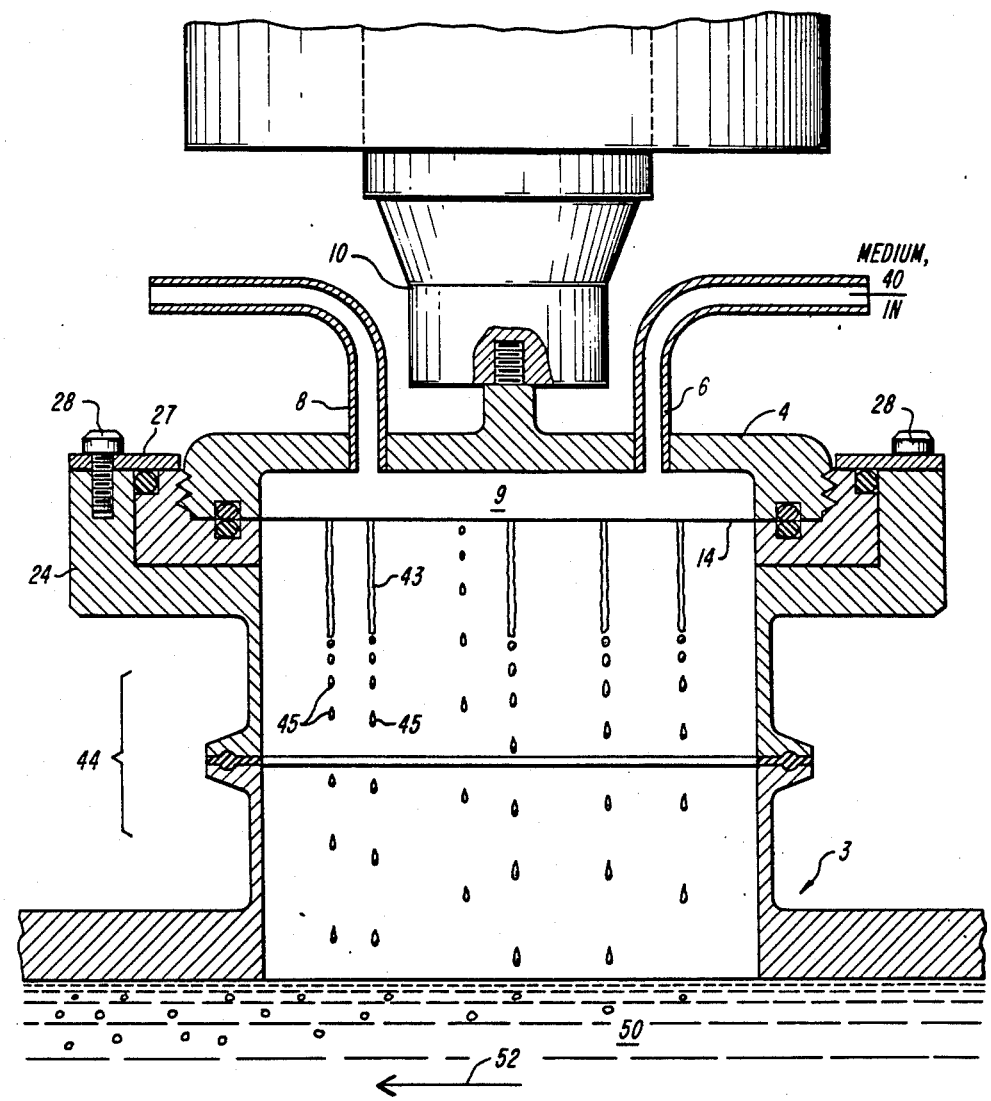
FIG. 2 shows a section of the assembled apparatus of FIG. 1.

The entire supply chamber structure consisting of the collar 18, orifice member 14, and cap 4 mount as a unit on a vessel platform 24 via annular flange 27 secured by cap screws 28 (shown in FIG. 2). Supply chamber assembly 2 is sealed against the platform 24 with O-rings 30, 32 nested in grooves formed in the corresponding structures. The various housing pieces 4,18,24 are preferably formed of a surgical grade stainless steel such as a 316L material, and are finished, for example with a 240 grit abrasive followed by an electropolishing finish operation. The gaskets 22a,22b,30,32 are preferably formed of an inert, non-bleeding material of the type used for pressure seals, for example the fluoroelastomer material sold commercially under the trade name Viton and widely used in the biological industry, or a silicone elastomer. Below the platform 24 is a collection vessel 3 to which the vessel platform 24 is connected via a triclamp which fits about a bevelled flange area 36 thereof. A gasket 38 seals the connection.

As shown in FIG. 1, the supply chamber 2 with its attached vibration unit is adapted for fitting over a vessel, with a fitting of a type conventionally used in a biological culture system. The vessel 3 serves as an encapsulating vessel for receiving the formed droplets and treating them with a hardening treatment fluid. The vibration generator 10 may be a piezoelectric driving unit. One suitable unit is sold by the Wilcoxon Company as their model number F7/F4/Z7. Other piezo units are readily available commercially, and other types of drive units, such as an electromagnetic driver or a motor driven eccentric cam vibrator may also be used.

Turning now to FIG. 2, there is shown a perspective cross section of the apparatus of FIG. 1. Identical parts are identically numbered therein. As shown in FIG. 2, a pressurized flow of the medium 40 which is to be encapsulated is provided through the inlet port 6 into the relatively shallow interior space 9 of the supply chamber (2 of FIG. 1). In the preferred embodiment, space 9 has a depth between its roof and the orifice member of approximately 6 millimeters. There is thus a negligible hydrostatic pressure gradient, and the cap member is strongly coupled through the chamber to the orifice member 14, which is a thin diaphragm-like member. Medium 40 is driven through the orifice member 14 in part by pressure and in part by the mechanical transport action of the sonic vibration applied to the chamber by vibrator 10, forming thin columns 43. The columns 43 break up into droplets 45 having a substantially uniform diameter.

When the medium passes through the member 14, standing wave in the columns of medium atomize the material into droplets 45. The atomized droplets 45 descend through the neck 44 defined by vessel platform 24 and the vessel coupling, into the collection vessel 3 where they contact a body of treatment fluid 50 such as the calcium chloride or other divalent metal hardening solution, as described in the aforesaid U.S. Pat. No. 4,386,895. The neck region 44 between the member 14 and the surface of a body of treatment fluid 50 in the collection vessel is maintained at a slight supra-atmospheric pressure by a vent, and has a vertical dimension in the range of 3-5 cm, which is just sufficient to allow atomizing breakup of the extruded column-like jets 43 of medium 40. Collection vessel 3 may comprise a portion of a circulation loop, wherein the fluid 50 is carried along a flow path indicated by arrow 52 to a filter or other separator for harvesting, so that the hardened microcapsules are continuously removed from the collection fluid.

In a preferred embodiment, vessel 3 is a stirred reactor vessel with an extremely low height to diameter ratio relative to conventional reactors. Multiple filter elements result in a high flow rate of treatment fluid through the vessel while decreasing mechanical damage to the capsules during solution removal. The supra-atmospheric pressure prevents the entry of external contaminants into the system.

Figure 3:
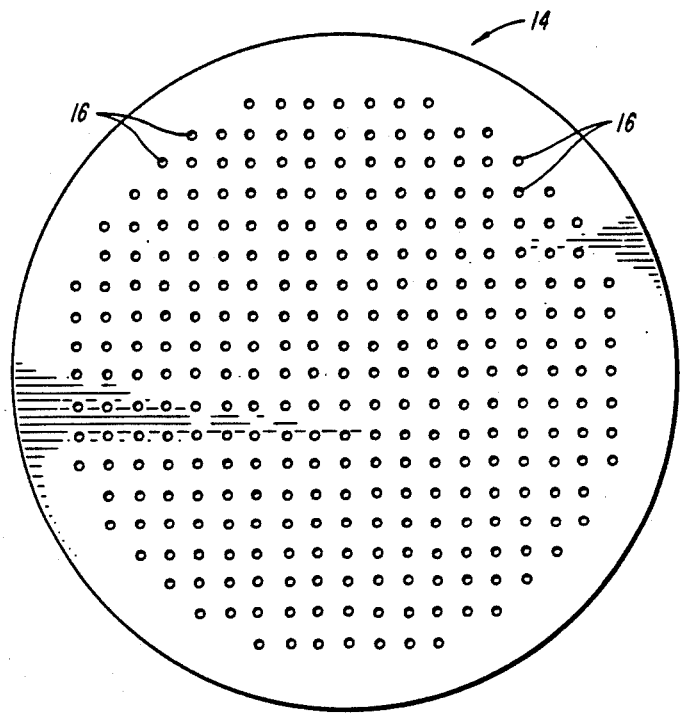
FIG. 3 shows a top view of the orifice member of the embodiment of FIGS. 1 and 2.

FIG. 3 is a top view of the orifice member 14 of FIG. 1. As shown, orifice member 14 comprises a thin planar portion having a plurality of holes or orifices 16 evenly spaced throughout a central region thereof. The spacing between holes 16 is selected to be small enough to provide a large number of holes to optimize throughflow of material, yet dispersed enough to prevent clumping of the atomized droplets which have passed therethrough. The diameter of the holes 16 is selected to provide droplets of the desired size, and will vary somewhat depending upon the viscosity of the medium 40, the drive frequency of vibrator 10, and the operating pressure difference of the apparatus across the orifice member 14. The operating pressure must be low enough to avoid damage to the viable material of the medium 40.

One prototype apparatus having a structure as shown in FIG. 1 was operated with a 1.6% aqueous sodium alginate solution having a viscosity of 80 centipoise. The apparatus had a supply chamber and orifice member diameter of approximately 9 cm., and was attached to a 10 cm port of a collection vessel. Cell medium was supplied to the inlet at a pressure of up to approximately 2.7 atmospheres by pressurizing a supply tank with nitrogen to force the fluid through a high pressure delivery tube to inlet 6.

Under these conditions, the apparatus converted the cell medium to droplets at a rate of between 5 and 10 millilitres/minute per orifice. The vibrational drive was supplied by a piezoelectric vibrator operated at a 1000 Hz frequency with a sine wave input having a drive power of approximately 100 watts. The orifice size was 300 microns. The droplets so produced had a diameter of 600 microns, with over 90% of the droplets lying between 550 and 650 microns. These characteristics constitute a significant improvement, both as to droplet uniformity and rate of droplet production. For example, an orifice member in a ten centimeter diameter supply chamber with 100-200 orifices converts between one-half and two liters/minute of medium into microcapsules.

A preferred apparatus for the invention having been thus disclosed, other variations of apparatus, and of methods of practicing according to the invention will occur to those skilled in the art, and all such variations are intended to be within the scope of the invention, as defined by the following claims.

What is claimed is:

1. Apparatus for forming microcapsules of a desired size from a fluid medium containing living culture material by the atomization of the medium, such apparatus comprising:
   a flow chamber for flowing the medium therethrough and including
   (a) a flow cap, having an inlet port and
   (b) a wall member having first and second opposing sides, said wall member being attached to the cap such that the cap and said first side define said chamber, said wall also having a plurality of orifices formed therethrough;
   pressure means, for pressurizing the flow chamber to drive the medium through the orifices;

vibration means for vibrating the chamber to atomize the medium flowing through the orifices; and means for coupling the apparatus to a collection vessel on the second side of the wall so as to deliver to the collection vessel said atomizing flow.

2. Apparatus according to claim 1, wherein the orifices have a diameter in the range of approximately 100-500 microns.

3. Apparatus according to claim 2, wherein the pressure means includes means for providing pressure in the range of approximately 1 to 4 atmospheres.

4. Apparatus according to claim 3, wherein the wall member is a perforated diaphragm.

5. Apparatus according to claim 4, further including a collection vessel and means for flowing treatment fluid through the collection vessel.

6. Apparatus according to claim 1, wherein the wall member is a perforated diaphragm.

7. Apparatus according to claim 6, wherein the cap and wall define a roof and a floor, respectively, of the chamber and wherein the distance between the roof and the floor is less than approximately one-quarter of the diameter of the diaphragm.

8. A method for forming microcapsules of a fluid medium containing living culture material by the atomization of the medium and the treatment of atomized droplets thereof with a treatment fluid, such method comprising the steps of:

flowing the medium through an inlet port into a flow chamber having a flow cap and a wall member having first and second opposing sides, said wall member being attached to the cap such that the cap and said first side define said chamber, said wall also having a plurality of orifices formed therethrough;

providing pressure in said chamber to drive the medium through the orifices, vibrating the chamber to atomize the medium driven through the orifices, and receiving said atomized flow in a vessel of the treatment fluid on the second side of the wall.

9. The method of claim 8, wherein the orifices have a diameter in the range of approximately 100-500 microns.

10. The method of claim 9, wherein the wall member is a perforated diaphragm.

11. The method of claim 10, further including the step of flowing treatment fluid through the collection vessel.

12. The method of claim 11, wherein the step of providing pressure includes providing pressure in the range of approximately 1 to 4 atmospheres.

13. Apparatus for the production of sub-millimeter droplets from a fluid medium containing living culture material, such apparatus comprising:

a shallow cap having a roof portion, a vibrator affixed to the cap, an orifice member affixed to the cap opposite the roof portion so as to define, together with the cap, a closed chamber, said orifice member including one or more orifices therethrough of a diameter functionally related to a desired droplet diameter, spacing means for providing a free-fall space below said orifice member, and pressure means for pressurizing the chamber so as to drive the medium therein as a fluid stream through the orifices whereby the droplets are produced by vibration of the fluid stream in the free fall space.

14. Apparatus according to claim 13 wherein the orifice member is removably and replaceably affixed to the cap.

15. Apparatus according to claim 14, further including a treatment vessel, coupled to the spacing means, for receiving said droplets and treating them with a treatment fluid.

16. Apparatus according to claim 15, wherein the diameter of the orifices is approximately one-half of the desired droplet diameter.

* * * * *